US010631876B2

(12) United States Patent
Machill (10) Patent No.: US 10,631,876 B2
(45) Date of Patent: Apr. 28, 2020

(54) MEDICAL DEVICE

(71) Applicant: Aesculap AG, Tuttlingen (DE)

(72) Inventor: Martin Machill, Rietheim-Weilheim (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 16/135,162

(22) Filed: Sep. 19, 2018

(65) Prior Publication Data

US 2019/0015112 A1 Jan. 17, 2019

Related U.S. Application Data

(63) Continuation of application No. PCT/EP2017/056903, filed on Mar. 23, 2017.

(30) Foreign Application Priority Data

Mar. 23, 2016 (DE) .......................... 10 2016 105 431

(51) Int. Cl.
| | |
|---|---|
| *F16C 29/04* | (2006.01) |
| *A61B 17/14* | (2006.01) |
| *B27B 19/00* | (2006.01) |
| *F16C 33/40* | (2006.01) |
| *A61B 17/16* | (2006.01) |
| *B23D 51/02* | (2006.01) |

(52) U.S. Cl.
CPC .......... *A61B 17/144* (2016.11); *A61B 17/162* (2013.01); *B23D 51/02* (2013.01); *B27B 19/006* (2013.01); *F16C 29/04* (2013.01); *F16C 33/40* (2013.01); *A61B 17/1624* (2013.01); *F16C 2316/10* (2013.01)

(58) Field of Classification Search
CPC ...... F16C 29/04; F16C 29/045; F16C 29/046; F16C 31/04; F16C 33/40; F16C 33/405; F16C 2316/10; F16C 2322/50; A61B 17/14; A61B 17/142; A61B 17/147; A61B 17/162; A61B 17/1624
See application file for complete search history.

(56) References Cited

U.S. PATENT DOCUMENTS

| | | | | |
|---|---|---|---|---|
| 3,674,324 | A | * | 7/1972 | Schweizer et al. ..... F16C 31/04 384/49 |
| 4,252,121 | A | | 2/1981 | Arnegger |
| 5,248,203 | A | | 9/1993 | Agari |

(Continued)

FOREIGN PATENT DOCUMENTS

| | | |
|---|---|---|
| DE | 6901870 | 7/1972 |
| DE | 2227312 | 1/1974 |

(Continued)

*Primary Examiner* — Phillip A Johnson
(74) *Attorney, Agent, or Firm* — Lipsitz & McAllister, LLC (57) ABSTRACT

The invention relates to a medical device with a machine element mounted so as to be linearly movable and at least one linear guide, comprising at least one ball bearing and defining a longitudinal axis, for guiding a linear movement of the machine element parallel to the longitudinal axis, said at least one ball bearing comprising a plurality of balls which are movably held in corresponding ball holders and which guide the machine element, wherein the plurality of ball holders are constructed in the form of elongated holes.

25 Claims, 6 Drawing Sheets

(56) References Cited

U.S. PATENT DOCUMENTS

| | | | | |
|---|---|---|---|---|
| 5,622,434 A * | 4/1997 | Takahashi | ............... | F16C 29/04 |
| | | | | 384/16 |
| 5,716,140 A | 2/1998 | Kondo et al. | | |
| 2003/0219184 A1 * | 11/2003 | Rio | ................... | A61B 17/1624 |
| | | | | 384/523 |
| 2013/0204255 A1 * | 8/2013 | Milburn | ............... | A61B 17/142 |
| | | | | 606/82 |
| 2017/0138398 A1 * | 5/2017 | Niedermeier | ............. | B23C 3/00 |

FOREIGN PATENT DOCUMENTS

| | | |
|---|---|---|
| DE | 2849760 | 6/1979 |
| DE | 3500445 | 7/1986 |
| DE | 4228579 | 3/1993 |
| DE | 10221976 | 12/2003 |
| DE | 202008015070 | 4/2010 |
| DE | 102014225134 | 11/2015 |
| EP | 2208901 | 7/2010 |
| JP | 468483 | 3/1971 |
| JP | 5215645 | 2/1977 |
| JP | 02221713 | 9/1990 |
| JP | 2014001748 | 1/2014 |

\* cited by examiner

MEDICAL DEVICE

CROSS-REFERENCE TO RELATED APPLICATIONS

This application is a continuation of international application number PCT/EP2017/056903 filed on Mar. 23, 2017 and claims the benefit of German application number 10 2016 105 431.3 filed on Mar. 23, 2016, which are incorporated herein by reference in their entirety and for all purposes.

FIELD OF THE INVENTION

The present invention relates to a medical devices generally, and more specifically to a medical device with a machine element mounted so as to be linearly movable and at least one linear guide, comprising at least one ball bearing and defining a longitudinal axis, for guiding a linear movement of the machine element parallel to the longitudinal axis, the at least one ball bearing comprising a plurality of balls which are movably held in corresponding ball holders and which guide the machine element.

BACKGROUND OF THE INVENTION

The linear guides available on the market for medical devices of the kind described at the outset are usually constructed such that the balls are embedded in corresponding ball holders in the form of bores of a bearing or ball cage, hereinafter also referred to only as bearing cage. In particular, moving the machine element back and forth at a high oscillation frequency is a problem with such medical devices. The bearing cage is moved with it with an oscillating movement back and forth, also referred to as reciprocating movement. Owing to the mass inertia, at the reversal point of the oscillating movement a sliding or pushing of the balls may occur on their respective running partners, for example, the machine element itself. As a result, the balls may wear in an undesired manner, thereby causing a quality of the linear guidance to suffer significantly and a service life of the device to be reduced.

SUMMARY OF THE INVENTION

In an aspect of the invention, a medical device with a machine element mounted so as to be linearly movable and at least one linear guide, comprises at least one ball bearing and defines a longitudinal axis, for guiding a linear movement of the machine element parallel to the longitudinal axis. Said at least one ball bearing comprises a plurality of balls which are movably held in corresponding ball holders and which guide the machine element. The plurality of ball holders are constructed in the form of elongated holes

BRIEF DESCRIPTION OF THE DRAWING FIGURES

The foregoing summary and the following description may be better understood in conjunction with the drawing figures. There are shown in.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a medical device with a machine element mounted so as to be linearly movable and at least one linear guide, comprising at least one ball bearing and defining a longitudinal axis, for guiding a linear movement of the machine element parallel to the longitudinal axis, said at least one ball bearing comprising a plurality of balls which are movably held in corresponding ball holders and which guide the machine element, wherein the plurality of ball holders are constructed in the form of elongated holes The solution proposed in accordance with the invention enables, in particular, a movement of the balls in the ball holders to be decoupled from a movement of the ball holders. Unlike with conventional linear guides in which the balls are arranged in bores of a bearing cage, the balls can move back and forth in the elongated hole-shaped ball holders and thus roll on one or both of the sliding partners, for example, the guided machine element. With corresponding dimensions of the ball holders, in particular, a corresponding length of the elongated holes, a bearing cage comprising the ball holders can thus remain substantially unmoved, more particularly, in spite of a movement of the machine element parallel to the longitudinal axis. In this way, wear of the linear guide can be minimized and, consequently, a service life thereof and of the medical device increased. The elongated holes thus make it possible, in particular, for the masses to be moved to be reduced. This could also be achieved by the bearing cage not being constructed from a steel, but from a lighter material, for example, a plastic material or from a ceramic material. However, in particular, in the case of plastic materials, wear is relatively high, and ceramic materials are only producible for this purpose with a high degree of expenditure and are expensive. Accordingly, the invention makes it possible, in particular, to use conventional bearing cages made of steel, without having to move these. A mass of the bearing cage is thus of practically no significance for an oscillating movement of the machine element and its linear guidance. Here an elongated hole is to be understood, in particular, as a through-hole having a greater extent in a first direction than in a second direction transversely to the first direction, so that the ball mounted in the elongated hole can be moved substantially only parallel to the first direction, i.e., can only roll back and forth. Furthermore, the arrangement of the balls in ball holders constructed in the form of elongated holes makes it easier to clean the medical device. Cleaning liquid can get in between the balls and the ball holders of a bearing cage much better.

It is expedient for the machine element to comprise at least one rotationally symmetrical machine element section which is guided in the at least one linear guide. The rotationally symmetrical machine element section enables, in particular, also a rotation relative to the linear guide if this should be necessary. In addition, a construction of a ball bearing surrounding this machine element section can be easily implemented.

The rotationally symmetrical machine element section is particularly easy to manufacture if it has a circular cross section.

For special kinds of medical devices it may be expedient for the machine element to be constructed in the form of a ram or a piston. For example, oscillating saws in the form of jigsaws can thus be easily constructed.

The construction of the medical device can be further simplified by the at least one ball bearing comprising a bearing cage and by the plurality of ball holders being formed in the bearing cage. Owing to the configuration of the bearing cage, the balls can then be arranged in the desired manner, so that they can guide the oscillatingly moved machine element in the desired manner.

It is advantageous for the elongated holes to each define an elongated hole longitudinal axis, and for the elongated hole longitudinal axis to extend parallel or transversely to the longitudinal axis. If, in particular, no rotation of the bearing cage about the longitudinal axis is desired, it is advantageous for the elongated holes to be aligned with their elongated hole longitudinal axis parallel to the longitudinal axis. However, a so-called running-in of balls on the machine element, i.e., the formation of abrasive marks owing to a sliding movement instead of the desired rolling movement of the balls relative to the machine element can be prevented by the elongated hole longitudinal axes of the ball holders extending transversely to the longitudinal axis. Here transversely means, in particular, not perpendicularly, i.e., at an angle between 0° and 90°, but at an angle which is preferably significantly smaller than 90°, in particular, smaller than 50°.

In order to enforce a defined rotation of the bearing cage about the longitudinal axis, it is advantageous for the elongated hole longitudinal axes to include with the longitudinal axis an angle of twist in a range of from 0° to approximately 30°. Such a configuration makes it possible, in particular, with an oscillating movement of the machine element, to also rotate the bearing cage about the longitudinal axis by a movement of the balls in the elongated hole-like ball holders.

In accordance with a further preferred embodiment of the invention, it may be provided that the plurality of elongated holes have a free length of movement for the ball movably arranged in each of them, and that the free length of movement corresponds to at least half of a stroke of the machine element relative to the linear guide. A stroke, also referred to as length of stroke, of the machine element corresponds to a distance along which the machine element oscillates back and forth owing to a movement parallel to the longitudinal axis. The proposed free length of movement of at least half of a stroke of the machine element ensures that the balls are not forced to enter into contact with inner end faces of the elongated holes of the ball holders that face each other when they roll on both of their bearing partners, i.e., in particular, the machine element. A length of the elongated holes can thus be minimized and nevertheless the desired effect achieved, namely, in particular, that of avoiding movement of the bearing cage itself and of improving cleanability of the ball bearing.

In order to further minimize wear of the linear guide, it is expedient for the elongated holes to have a free length of movement which is at least 10% greater than half of the stroke. In particular, the free length of movement can be at least 30% greater than half of the stroke. Contact of the balls with inner end faces of the elongated holes of the ball holders can thus be substantially reliably avoided.

The bearing cage is preferably arranged on the linear guide for rotation about the longitudinal axis. Run marks of the balls on the machine element owing to its oscillating movement back and forth can thus be prevented from forming.

Furthermore, it may be advantageous for the least one ball bearing to comprise a bearing sleeve surrounding the bearing cage for limiting movement of the balls in the radial direction away from the longitudinal axis. The bearing sleeve may form, in particular, a bearing partner for the balls, on which these can roll. In addition, the ball bearing can thus be easily manufactured and inserted in desired openings on medical devices, for example, in recesses provided for the bearing sleeve. The balls can, therefore, roll, for example, on the machine element, on the one hand, and on the bearing sleeve, on the other hand, so that the machine element and the bearing sleeve can move over a length of stroke relative to each other, but the balls only move over the free length of movement relative to the machine element and to the bearing sleeve, with the length of movement corresponding to half of the length of stroke, and, consequently, to half of the stroke of the machine element relative to the linear guide.

It is advantageous for the plurality of elongated holes to have an elongated hole width transversely to their respective elongated hole longitudinal axis, and for the elongated hole width to decrease in the radial direction towards the longitudinal axis. In other words, the longitudinal holes taper in their width in the direction towards the longitudinal axis. As a result, they can be so constructed that the balls cannot fall out of the elongated holes in the direction towards the longitudinal axis. If the bearing cage is surrounded, for example, by the bearing sleeve, the balls can then be easily secured against falling out of the bearing cage, more particularly, inwardly in the direction towards the longitudinal axis by the decrease in the elongated hole width and outwardly in the direction away from the longitudinal axis by the bearing sleeve.

The balls can be easily secured in the ball holders against falling out in the direction towards the longitudinal axis by lateral delimitation surfaces of the plurality of elongated holes that face each other being inclined at a cone angle to each other.

It is expedient for the cone angle to be open facing away from the longitudinal axis. The balls can thus be easily secured in the elongated holes against falling out in the direction towards the longitudinal axis.

To enable optimal guidance of the machine element on the medical device, it is expedient for a wall thickness of the bearing cage to be smaller than a diameter of the plurality of balls. In particular, the wall thickness may correspond at most to half of a diameter of the plurality of balls. In this way, it is ensured that the balls can protrude from the bearing cage both in the direction towards the longitudinal axis and in the direction away from the longitudinal axis, in order to be able to roll, for example, on the one hand, on the machine element and, on the other hand, on the bearing sleeve.

In order that as good a guidance of the machine element as possible can be achieved, it is advantageous for the bearing cage to comprise at least two rows of holes axially spaced from each other in the circumferential direction in relation to its longitudinal axis and each comprising several elongated holes. The rows of holes thus form rings surrounding the longitudinal axis. If two bearing cages separate from each other are provided, each bearing cage may also comprise only one such hole ring or such a row of holes.

It is advantageous for the elongated holes of adjacent rows of holes to be arranged in alignment with or offset from one another. In particular, adjacent rows of holes can be arranged offset from one another, in particular, such that elongated holes of a second row of holes are arranged offset by a circumferential angle from the elongated holes of an adjacent first row of holes, with the circumferential angle corresponding to half of an angular spacing in relation to the longitudinal axis between adjacent elongated holes of the first and/or second row of holes. Particularly compact, low-wear ball bearings can thereby be constructed.

In accordance with a further preferred embodiment of the invention, it may be provided that the linear guide comprises two or more ball bearings separate from each other with at least one bearing cage each, and that each bearing cage has at least one row of holes with several elongated holes arranged in the circumferential direction in relation to its longitudinal axis. This configuration of the linear guide makes it possible, in particular, to mount the machine element in a material-saving manner, in particular, when it exceeds a certain length. It is then possible, for example, for ball bearings with one or more rows of holes to be provided only in the end areas of the machine element. The further the ball bearings are arranged from each other, the more stable is an axial guidance of the machine element.

It is advantageous for the bearing cage to comprise a radial securing device for preventing the balls from exiting from the respective ball holders in a direction away from the longitudinal axis or in a direction towards the longitudinal axis. The radial securing device makes it possible, in particular, to handle the ball bearing as a whole, for example, for assembly thereof on the medical device, without the balls of the ball bearing being able to exit from the ball holders. The radial securing device may, in particular, be so constructed that the balls cannot fall out of the ball holders, but protrude far enough from the ball holders that they can enter into contact, for example, with the machine element and/or the bearing sleeve and can roll on these without the bearing cage touching the machine element or the bearing sleeve.

The radial securing device can be constructed in a simple way if it comprises bent edges of the ball holders. Bending the edges is to be understood, in particular, as meaning that these are reshaped such that a minimal width of the ball holders is smaller than a diameter of the balls, so that these cannot fall out. In particular, the bending of the edges of the ball holders can take place after the balls have first been inserted in the ball holders with edges that are not bent. The bending of the edges then takes place, for example, during assembly of the ball bearing.

The balls can be secured in the ball holders in a simple way if the radial securing device comprises a cover sleeve, the inner diameter of which corresponds to an outer diameter of the bearing cage, and if the cover sleeve comprises a plurality of elongated hole-like cover through-holes, the width of which is smaller than a ball diameter. Such a cover sleeve serves substantially the same purpose as bent edges of the ball holders. The cover through-holes of the cover sleeve are dimensionally so configured that the ball located in the ball holder cannot pass through the cover through-holes. Furthermore, provision may also optionally be made for securing the bearing sleeve and/or the cover sleeve axially on the bearing cage. For this purpose, for example, the bearing sleeve, after assembly of the balls in the ball cage, can be secured in the direction of stroke, i.e., parallel to the longitudinal axis, such that at least a first end of the bearing sleeve is reshaped, for example, by flanging, all around or at least in a section thereof inwardly, i.e., in the direction towards the longitudinal axis. A second end of the bearing sleeve could be reshaped as well or, alternatively, it could also already have a firm collar as stop. The cover sleeve can be axially secured to the bearing cage in an analogous way. Owing to the reshaping at at least one of the two ends of the bearing sleeve and/or the cover sleeve, a diameter of the bearing sleeve and/or the cover sleeve is reduced, so that removal of the bearing cage fitted with the balls parallel to the longitudinal axis is prevented. The thus formed unit, namely the ball cage with the balls and the bearing sleeve and/or the cover sleeve, can be easily handled as group of components and, if required, exchanged when servicing the medical device. Alternatively, a capping of the bearing sleeve and/or the cover sleeve may also be provided, more particularly, with one or two caps in the form of additional parts, which close openings of the bearing sleeve and/or or the cover sleeve facing in the direction of the longitudinal axis and thus prevent removal of the ball cage.

The linear guide can be constructed in a simple way if the bearing sleeve is arranged so as to surround the cover sleeve. For example, the balls can thus be inserted in the bearing holders and held in the bearing holders by pushing the cover sleeve onto the bearing sleeve.

Linear guides can be constructed in a simple and cost-effective manner if the at least one ball bearing is formed from a metal. In particular, the bearing cage can be formed from a metal. The metal may be, in particular, an instrument steel, which is preferably rustproof.

In order to be able to use the medical device as medical machine tool, it is expedient for the machine element to comprise a coupling device for releasable connection to a tool element. A tool element, for example, a saw blade or a milling head, can thus be coupled in a simple way to the machine element. If the tool element is worn or damaged, it can be separated from the machine element again in a simple way and replaced by a functioning tool element.

The medical device is expediently constructed in the form of a saw, a milling machine or a drilling machine. Such machines can be used, in particular, for surgical purposes.

Figure 1:
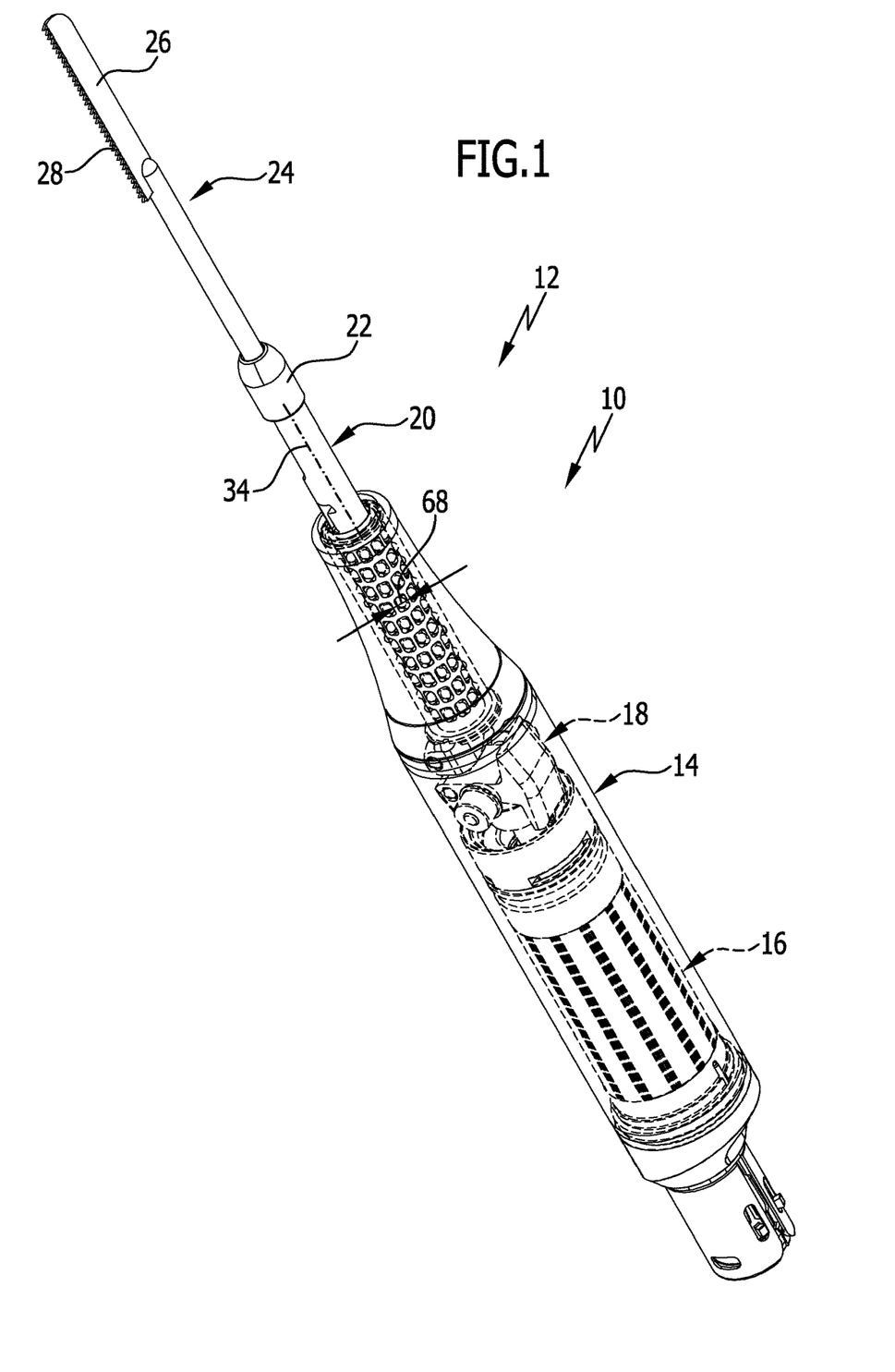
FIG. 1: a schematic, partially broken-open, perspective overall view of a medical device.
Figure 2:
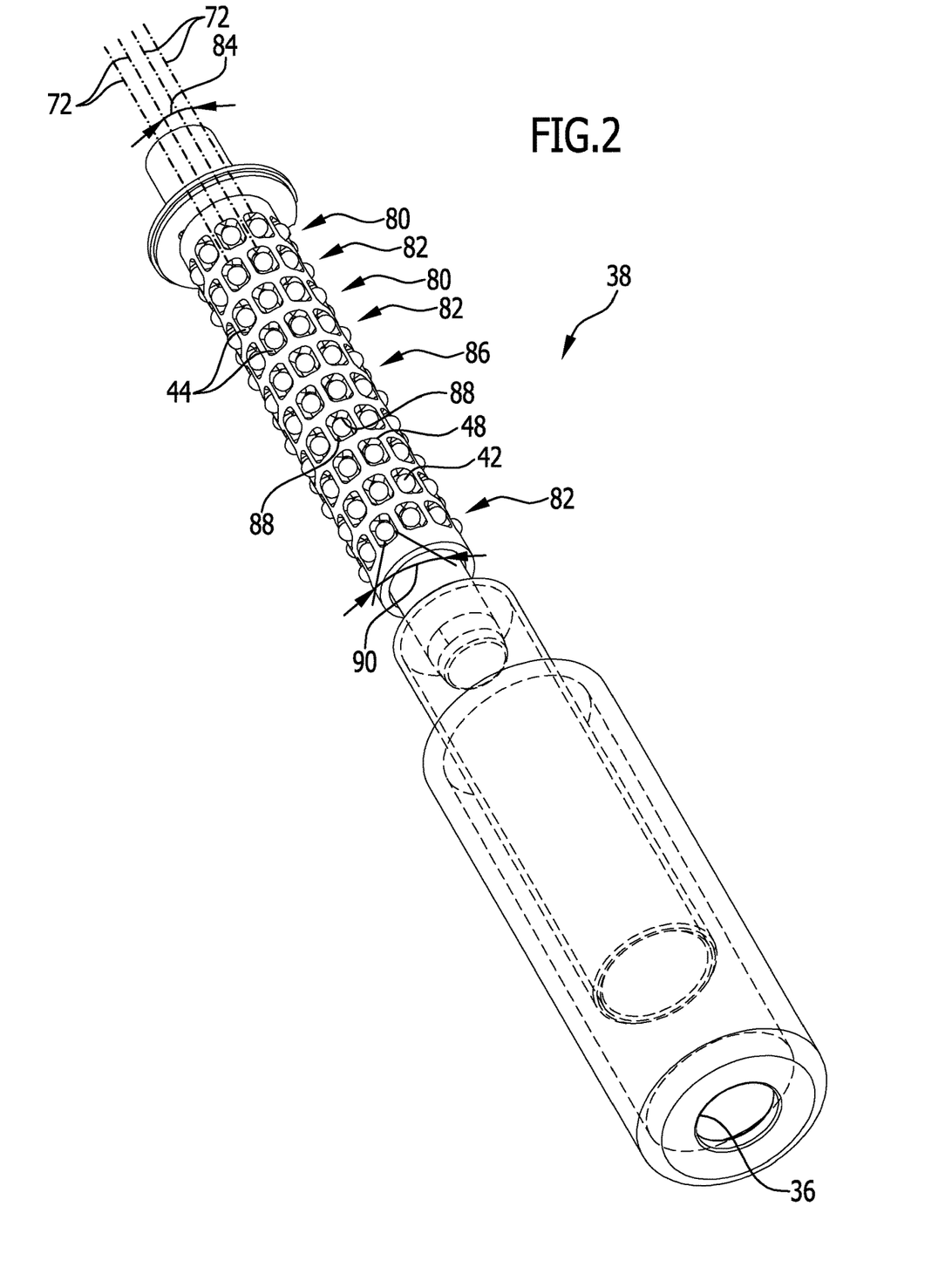
FIG. 2: a partially broken-open, exploded representation of part of the device from FIG. 1.
Figure 3:
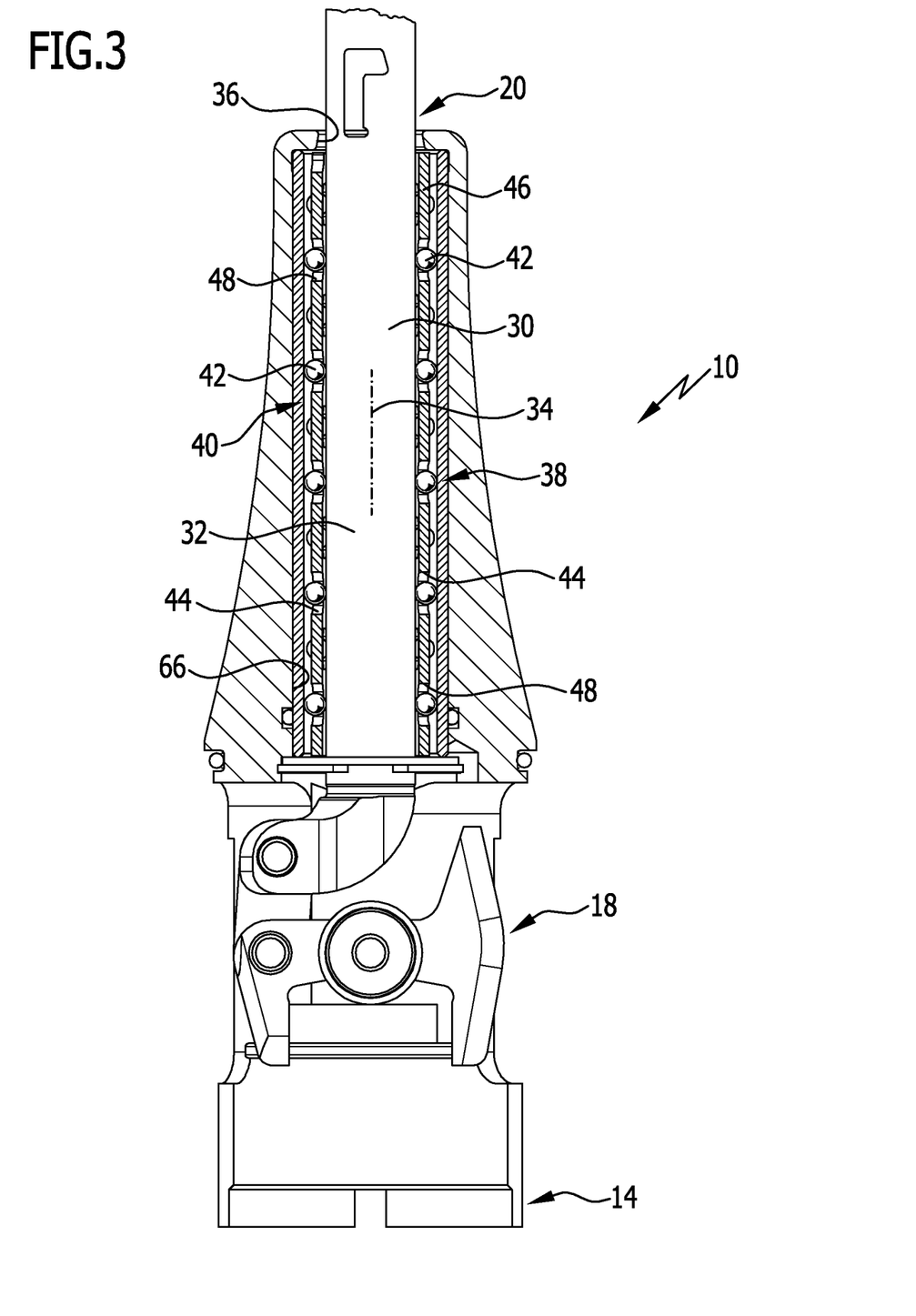
FIG. 3: a partially sectional view of the device from FIG. 1 in the area of a linear guide.
Figure 4:
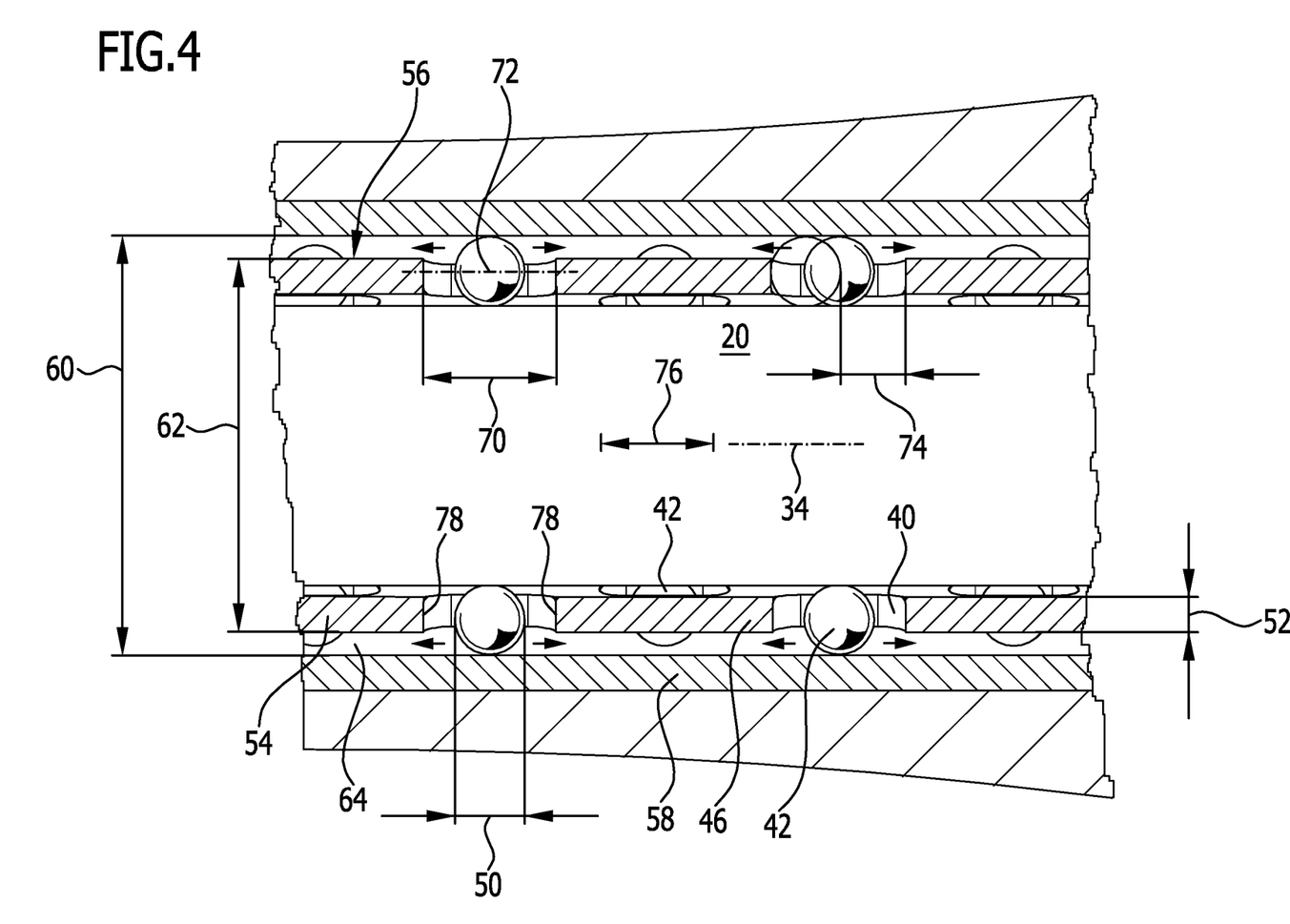
FIG. 4: an enlarged partial view of the assembly from FIG. 3.

An embodiment of a medical device, designated in its entirety by reference numeral 10, in the form of a jigsaw 12, is shown schematically in FIG. 1.

The device 10 comprises a housing 14 serving as handle, in which there is arranged a drive 16 in the form of an electric motor. This can be selectively supplied with electric energy mains-independently by means of a battery, not shown, in particular, a rechargeable battery, or mains-dependently by means of a mains cable electrically conductively connected to the drive 16.

A compressed-air motor or another sterilizable drive may be used instead of an electric motor.

A gearing 18 may be optionally coupled to the drive 16, in order, for example, to convert a rotation of a drive shaft, not shown, of the drive 16 into a linear oscillating movement.

There can be coupled to the gearing 18, in particular, a machine element 20 which comprises at its end facing away from the gearing 18 a coupling device 22 for releasable connection of the machine element 20 to a tool element 24.

Optionally, the machine element 20 may also be directly coupled to the drive 16. A coupling of the machine element 20 to a rotating bendable shaft could also be provided.

In the medical device 10 shown by way of example in FIG. 1, the tool element 24 is constructed in the form of a saw blade 26 with a row of teeth 28 comprising a plurality of teeth. The coupling device 22 may, in particular, be constructed in the form of a quick coupling so as to enable quick exchange of the saw blade 26, for example, when it is worn or it is to be replaced by another saw blade with teeth of a different shape.

The machine element 20 is constructed in the form of a ram 30 and has a rotationally symmetrical machine element section 32. A cross section thereof is circular. The machine element section 32 defines a longitudinal axis 34.

The machine element 20 is moved back and forth by the drive 16 in conjunction with the gearing 18 oscillatingly and parallel to the longitudinal axis 34.

In order to guide in a defined manner the machine element 20 protruding partially from a front part of the housing 14 so that it cannot enter into contact with a through-hole 36 which is formed coaxially with the longitudinal axis 34 and through which it passes, a linear guide 38 is arranged in the housing 14, more particularly, coaxially with the longitudinal axis 34.

The linear guide 38 comprises a ball bearing 40 with a plurality of balls 42 which are movably held or mounted in ball holders 44 so that, in particular, they can rotate about their ball center points.

The ball bearing 40 further comprises a ball or bearing cage 46 comprising the ball holders 44. The ball holders 44 are constructed in the form of elongated holes 48. These will be described in greater detail hereinbelow.

The balls 42 have a diameter 50 which is approximately twice as large as a thickness 52 of a wall 54 of the bearing cage 46 constructed in the form of an elongated sleeve 56.

The ball bearing 40 further comprises a bearing sleeve 58 arranged concentrically with the longitudinal axis 34 and surrounding the bearing cage 46. An inner diameter 60 of the bearing sleeve 58 is somewhat larger than an outer diameter 62 of the bearing cage 46. The inner diameter 60 and the outer diameter 62 are coordinated with each other in such a way that the balls 42 movably held in the ball holders 44 can roll on an inner wall surface 64 of the bearing sleeve 58.

The ball bearing 40 is inserted into a correspondingly constructed ball bearing retainer 66 in the front part of the housing 14.

The elongated holes 48 have a width 68 in the circumferential direction in relation to the longitudinal axis 34 and a length 70 in a direction parallel to the longitudinal axis 34. The elongated holes 48, therefore, each define an elongated hole longitudinal axis 72 extending parallel to the axis 34.

The length 70 is greater than the diameter 50 and is preferably selected such that a free length of movement 74, which is predetermined by the elongated holes 48 for the balls 42, corresponds at least approximately to half of a length of stroke 76 of the machine element 20. The free length of movement 74 is the difference between the length 70 and the diameter 50.

The length of stroke 76 corresponds to the distance that the machine element 20 is moved back and forth parallel to the longitudinal axis 34. The described relationship between the free length of movement 74 and the length of stroke 76 results on account of the balls 42 rolling, on the one hand, on the inner wall surface 64 and, on the other hand, on the machine element 20.

The elongated holes 48 do, however, preferably define a free length of movement 74 which is at least 10% greater than half of the length of stroke 76. In order to ensure that the balls 42 cannot strike end faces 78 of the elongated holes 48 that face each other, it is expedient for the free length of movement 74 to be chosen at least 30% greater than half of the length of stroke 76.

Owing to the balls 42 being able to move freely in the elongated holes 48 parallel to the elongated hole longitudinal axis 42 and ideally not striking the end faces 78 or coming to rest against these, which would have the unwanted result that they do not roll on the machine element 20 and the bearing sleeve 58, but slide along these, the bearing cage 46 is not moved parallel to the longitudinal axis 34 when the machine element 20 oscillates back and forth. Owing to the free movability of the balls 42 in the elongated holes, the bearing cage 46 does not have to be moved as well during the oscillating movement of the machine element 20. This has the advantage that the bearing cage 46 can also be produced from a heavy material, for example, a rustproof instrument steel, without increasing the wear of the linear guide 38. Owing to the bearing cage 46 not having to be moved, less energy is required for the oscillating movement of the machine element 20. It is, therefore, no longer a question of keeping the mass of the bearing cage 46 as low as possible.

If the ball holders 44 are constructed in the form of bores, as is known in the state of the art, while rolling on the machine element 20, the balls 42 move the bearing cage 46 along with them more or less synchronously with an oscillating movement of the machine element 20. As a result, it cannot be excluded that the balls 42 will become stuck in the ball holders 44, resulting in an undesired sliding movement of the balls 42, in particular, relative to the machine element 20 and possibly also to the bearing sleeve 58 and not in the actually desired rolling movement. An undesired effect of such a sliding movement is, however, that depressions may form in the machine element 20 and possibly also in the bearing sleeve 58. The risk of such undesired deformations of the machine element 20 and possibly also of the bearing sleeve 58 is practically eliminated by the construction of the ball holders 44 in the shape of elongated holes.

The ball bearing 40 can comprise, in particular, as shown in FIGS. 1 to 4, several rows of holes 80 and 82, each comprising several ball holders 44, which are formed on the bearing cage 46 in the circumferential direction in relation to the longitudinal axis 34.

The embodiment of the device 10 shown in FIGS. 1 to 4 comprises a total of ten rows of holes, more particularly, five rows of holes 80 and five rows of holes 82. The elongated holes 48 of the rows of holes 80 and 82 are each constructed so as to be uniformly distributed over the circumference. Each of the rows of holes 80 and 82 has the same number of ball holders 44.

The rows of holes 80 and 82 are constructed such that longitudinal axes of the elongated holes 48 of the row of holes 80 are arranged offset relative to the elongated hole longitudinal axes 72 of the elongated holes 48 of the row of holes 82 by half of a circumferential angle 84, which is defined by an angular spacing between the elongated hole longitudinal axes 72 of the elongated holes 48 of one of the two rows of holes 80 or 82.

Alternatively, the elongated holes 48 of the adjacent rows of holes 80 and 82 can be arranged in alignment with one another, i.e., such that the elongated hole longitudinal axes 72 of elongated holes 48 of adjacent rows of holes 80 and 82 coincide.

The linear guide 38 further comprises a radial securing device 86 for preventing the balls 42 from exiting from the respective ball holders 44 in a direction towards the longitudinal axis 34. The radial securing device 86 comprises lateral delimitation surfaces 88 which define the width 68 of the elongated holes 48 and, facing away from the longitudinal axis 34, are inclined to each other at a cone angle 90. The cone angle 90 can lie, in particular, in a range between 0° and approximately 45°.

Owing to the delimitation surfaces 88 inclined to each other, the width 68 decreases transversely to the elongated hole longitudinal axis 72 in the radial direction towards the longitudinal axis 34. Consequently, the ball holder 44 becomes narrower in the direction towards the longitudinal axis 34 and has a minimal elongated hole width 92 on passing through the wall 54 of the bearing cage 46, the minimal elongated hole width 92 being smaller than the diameter 50. It is thereby ensured that the balls 42 cannot fall out of the ball holders 44 in the direction towards the longitudinal axis 34.

Furthermore, the bearing sleeve 58 also forms part of the radial securing device 86 since it surrounds the bearing cage 46, as described above, such that movement of the balls 42 away from the longitudinal axis 34 is also restricted. The bearing sleeve 58, therefore, prevents the balls 42 from exiting from the ball holders 44 in a direction away from the longitudinal axis 34.

In addition or also as an alternative to delimitation surfaces inclined relative to each other, edges 94 joining the delimitation surfaces 88 and the inner wall surface 64 can be bent, i.e., somewhat in the direction towards a through-opening of the bearing cage 46, which is defined by the elongated hole 48, so that the minimal elongated hole width 92 is reduced somewhat, more particularly, at least to such an extent that it is smaller than the diameter 50. In this way, too, the balls 42 can be prevented from falling through in the direction towards the longitudinal axis 34.

Figure 5:
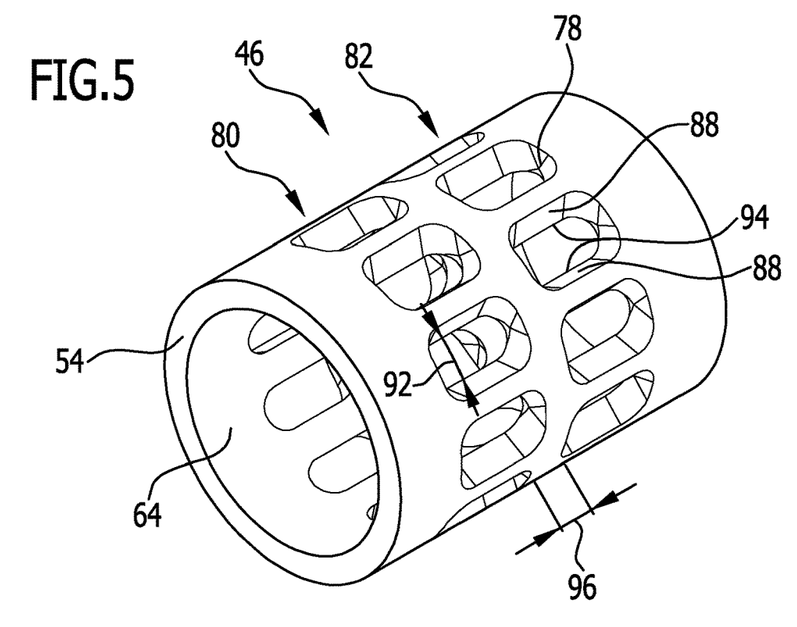
FIG. 5: a further embodiment of a bearing cage.

A further embodiment of a bearing cage 46 is shown schematically in FIG. 5. It is also constructed in the form of an elongated sleeve 56 and comprises only two rows of holes 80 and 82, the respective elongated holes 48 of which, as in the embodiment of the bearing cage 46 shown in FIGS. 1 to 4, are constructed offset through half of a circumferential angle 84 relative to one another.

The bearing cage 46 may, for example, be used to mount the machine element 20 only in sections of the machine element section 32 that are spaced from one another. In this way, a bearing cage 46 comprising significantly more than two rows of holes 80 and 82 can be dispensed with. Expenditure and costs involved in the manufacture of the device 10 can thereby be reduced.

Figure 6:
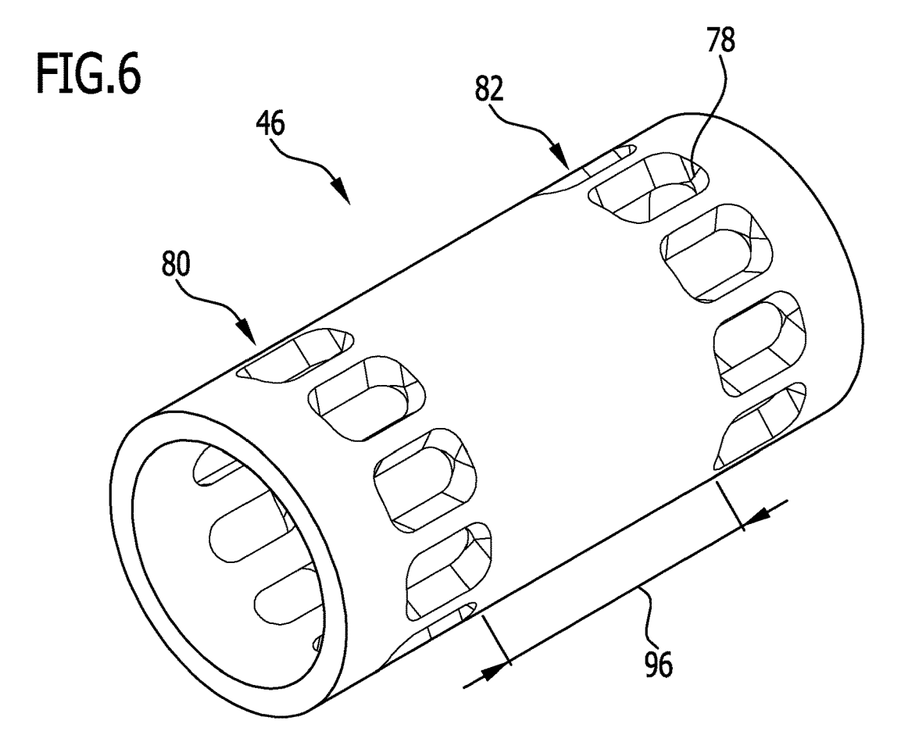
FIG. 6: a further embodiment of a bearing cage.

A particularly good guidance is achievable if, as in the embodiment of the bearing cage 46 shown schematically in FIG. 6, a spacing 96 of adjacent rows of holes 80 and 82 from each other is significantly increased. In particular, the spacing 96 can be a multiple of the length 70. In this way, the manufacture of the bearing cage 46 can be simplified and the number of balls 42 reduced.

Figure 7:
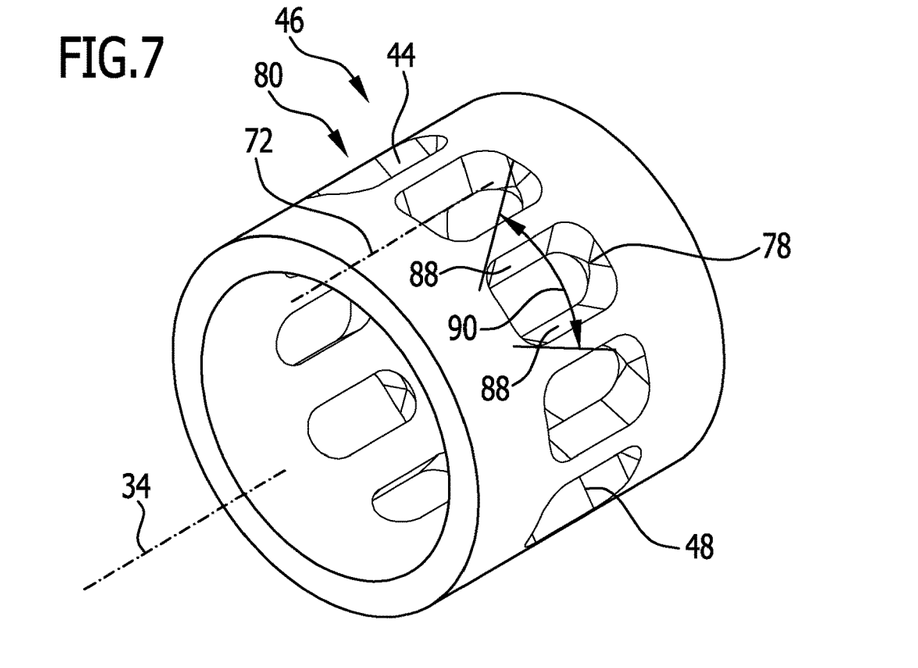
FIG. 7: a further embodiment of a bearing cage.

A further embodiment of a bearing cage 46 is schematically shown in FIG. 7. It comprises only a single row of holes 80 comprising several elongated holes 48. As in all of the embodiments of ball cages 46 described above, the elongated holes 48 are aligned with their elongated hole longitudinal axes 72 parallel to the longitudinal axis 34 of the bearing cage 46.

Two of the bearing cages 46 shown in FIG. 7 may, for example, be used for mounting the machine element 20 shown in FIGS. 1 to 4. These are then substantially positioned such that their rows of holes 80 surround the machine element 20 approximately at the positions where the rows of holes 80 and 82 spaced furthest from one another in the bearing cage 46 shown in FIGS. 1 to 4 are positioned. Significant costs for the manufacture of the bearing cage 46 and, therefore, also for the linear guide 38 can thereby be saved.

Figure 8:
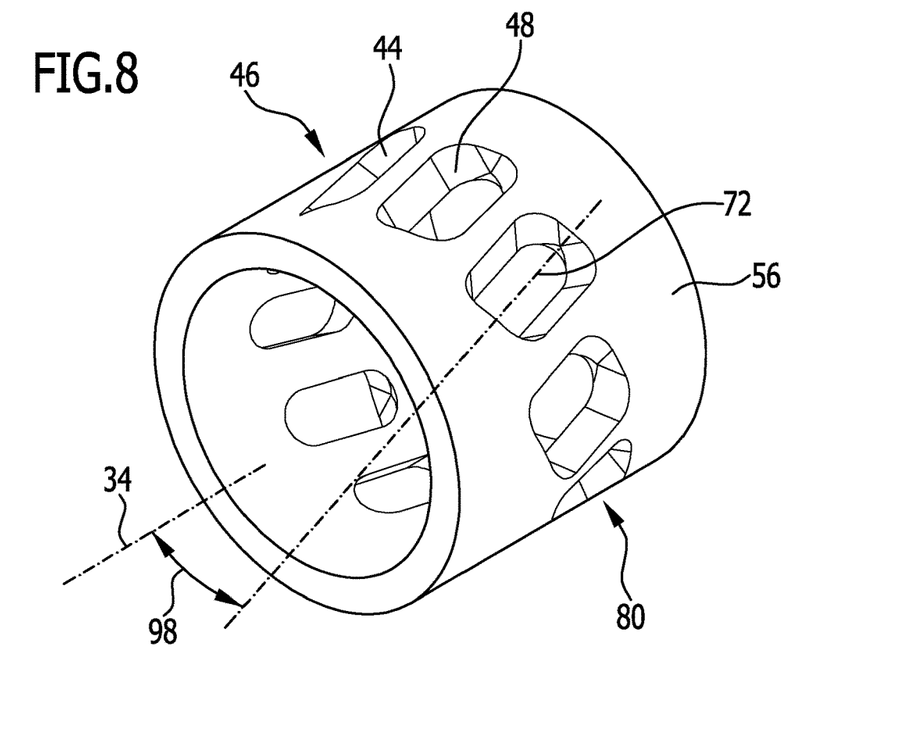
FIG. 8: a further embodiment of a bearing cage.

A further embodiment of a bearing cage 46 is shown schematically in FIG. 8. It again comprises a sleeve 56 having a row of holes 80 comprising several elongated holes 48. The elongated holes 48 are substantially identical in construction to the elongated holes in the embodiment of the bearing cage 46 shown in FIG. 7. The elongated holes 48 are, however, inclined with their elongated hole longitudinal axes 72 relative to the longitudinal axis 34 through an angle of twist 98. This preferably lies in a range between 0° and approximately 30°. The elongated holes 48 thus extending transversely or at an incline relative to the longitudinal axis 34 have the positive effect that as a result of movement of the machine element 20 back and forth parallel to the longitudinal axis 34, the bearing cage 46 is moved back and forth in the circumferential direction by the movement of the balls 42. This may result as a whole in a rotational movement of the bearing cage 46 about the longitudinal axis 34 or in an oscillating rotational movement of the bearing cage 46 about the longitudinal axis 34. The formation of friction or abrasive marks on the machine element 20 and possibly also on the bearing sleeve 58 parallel to the longitudinal axis 34 can thereby be prevented with a relatively high degree of reliability. If frictional movements of the balls 42 relative to the machine element 20 and possibly also to the bearing sleeve 58 should occur, these are, however, not always at identical positions, but are distributed over the circumference of the machine element 20 and possibly also the bearing sleeve 58.

Elongated holes 48 extending with the elongated hole longitudinal axes 72 at an incline relative to the longitudinal axis 34 can also be provided in bearing cages 46 with two or even more rows of holes 80 and 82, respectively, in particular, also in the other embodiments of FIGS. 1 to 7 described above, more particularly, either exclusively or also only partially.

The embodiments of bearing cages 46 and shapes of elongated holes 48 described above can essentially be combined in any way, so that an optimally adapted linear guide 38 can always be provided for guiding a machine element 20. In particular, the number of balls 42 and the number of ball bearings 40 used for guiding the machine element 20 can thus depend on the length of the machine element 20 or the machine element section 32 parallel to the longitudinal axis 34 and also on an oscillation frequency of the machine element 20.

In particular, all of the bearing cages 46 described above have in common that a sliding movement of the balls 42 mounted in them does not bring about movement of the bearing cages 46 parallel to the longitudinal axis 34. Consequently, as described above, they can also be produced from a material with a high mass density, for example, from a rustproof instrument steel. The bearing cages may, or course, also be formed from plastic materials or ceramic materials.

LIST OF REFERENCE NUMERALS

10 medical device
12 jigsaw
14 housing
16 drive
18 gearing
20 machine element
22 coupling device 24 tool element
26 saw blade
28 row of teeth
30 ram
32 machine element section
34 longitudinal axis
36 through-hole
38 linear guide
40 ball bearing
42 ball
44 ball holder
46 bearing cage
48 elongated hole
50 diameter
52 thickness
54 wall
56 sleeve
58 bearing sleeve
60 inner diameter
62 outer diameter
64 inner wall surface
66 ball bearing retainer
68 width
70 length
72 elongated hole longitudinal axis
74 free length of movement
76 length of stroke
78 end face
80 row of holes
82 row of holes
84 circumferential angle
86 radial securing device
88 delimitation surface
90 cone angle
92 elongated hole width
94 edge
96 spacing
98 angle of twist

What is claimed is:

1. A medical device, comprising:
a machine element mounted so as to be linearly movable, and
at least one linear guide, comprising at least one ball bearing and defining a longitudinal axis, for guiding a linear movement of the machine element back and forth at a high oscillation frequency parallel to the longitudinal axis,
said at least one ball bearing comprising a plurality of balls which are movably held in corresponding ball holders and which guide the machine element,
wherein:
the plurality of ball holders are constructed in the form of elongated holes, and
the elongated holes each define an elongated hole longitudinal axis, and
the elongated hole longitudinal axis extends transversely to the longitudinal axis, and
the elongated hole longitudinal axes include with the longitudinal axis an angle of twist in a range of between 0° to approximately 30°.

2. The medical device in accordance with claim 1, wherein the machine element comprises at least one rotationally symmetrical machine element section which is guided in the at least one linear guide.

3. The medical device in accordance with claim 2, wherein the rotationally symmetrical machine element section has a circular cross section.

4. The medical device in accordance with claim 1, wherein the machine element is constructed in the form of a ram or a piston.

5. The medical device in accordance with claim 1, wherein the machine element comprises at least one rotationally symmetrical machine element section which is guided in the at least one linear guide, wherein the at least one ball bearing comprises a bearing cage, and wherein the plurality of ball holders are formed in the bearing cage.

6. The medical device in accordance with claim 5, wherein at least one of:
a) a wall thickness of the bearing cage is smaller than a diameter of the plurality of balls,
or
a wall thickness of the bearing cage corresponds at most to half of a diameter of the plurality of balls,
and
b) the bearing cage comprises at least two rows of holes extending in the circumferential direction in relation to a longitudinal axis of the bearing cage and each comprising several elongated holes, the at least two rows being axially spaced from each other,
or
the bearing cage comprises at least two rows of holes extending in the circumferential direction in relation to a longitudinal axis of the bearing cage and each comprising several elongated holes, the at least two rows being axially spaced from each other, wherein elongated holes of adjacent rows of holes are arranged in alignment with or offset from one another.

7. The medical device in accordance with claim 6, wherein the linear guide comprises two or more ball bearings separate from each other with at least one bearing cage each, and wherein each bearing cage has at least one row of holes with several elongated holes arranged in the circumferential direction in relation to the longitudinal axis of the bearing cage.

8. The medical device in accordance with claim 7, wherein the bearing cage comprises a radial securing device for preventing the balls from exiting from the respective ball holders in a direction away from the longitudinal axis and/or in a direction towards the longitudinal axis.

9. The medical device in accordance with claim 8, wherein the radial securing device comprises bent edges of the ball holders.

10. The medical device in accordance with claim 9, wherein the radial securing device comprises a cover sleeve, the inner diameter of which corresponds to an outer diameter of the bearing cage, and wherein the cover sleeve comprises a plurality of elongated hole-like cover through-holes, the width of which is smaller than a ball diameter, and wherein the bearing sleeve is arranged so as to surround the cover sleeve.

11. The medical device in accordance with claim 8, wherein the radial securing device comprises a cover sleeve, the inner diameter of which corresponds to an outer diameter of the bearing cage, and wherein the cover sleeve comprises a plurality of elongated hole-like cover through-holes, the width of which is smaller than a ball diameter.

12. The medical device in accordance with claim 5, wherein the bearing cage comprises a radial securing device for preventing the balls from exiting from the respective ball holders in a direction away from the longitudinal axis and/or in a direction towards the longitudinal axis.

13. The medical device in accordance with claim 1, wherein the plurality of elongated holes have a free length of movement for the ball movably arranged in each of them, and wherein the free length of movement corresponds to at least half of a stroke of the machine element relative to the linear guide.

14. The medical device in accordance with claim 1, wherein the plurality of elongated holes have a free length of movement for the ball movably arranged in each of them, and wherein the free length of movement corresponds to at least half of a stroke of the machine element relative to the linear guide, and wherein the elongated holes have a free length of movement which is:
   a) at least 10% greater than half of the stroke, or
   b) at least 30% greater than half of the stroke.

15. The medical device in accordance with claim 14, wherein:
   the at least one ball bearing comprises a bearing cage, and at least one of:
   a) the bearing cage is arranged on the linear guide for rotation about the longitudinal axis and
   b) the at least one ball bearing comprises a bearing sleeve surrounding the bearing cage for limiting movement of the balls in a radial direction away from the longitudinal axis.

16. The medical device in accordance with claim 1, wherein the plurality of elongated holes have an elongated hole width transversely to the longitudinal axis of the respective elongated hole, and wherein the elongated hole width decreases in a radial direction towards the longitudinal axis.

17. The medical device in accordance with claim 16, wherein lateral delimitation surfaces of the plurality of elongated holes that face each other are inclined at a cone angle to each other.

18. The medical device in accordance with claim 17, wherein the cone angle is open facing away from the longitudinal axis.

19. The medical device in accordance with claim 1, wherein at least one of:
   a) the at least one ball bearing is formed from a metal, or
   the at least one ball bearing is formed from steel, or
   the at least one ball bearing comprises a bearing cage and the bearing cage is formed from a metal, or
   the at least one ball bearing comprises a bearing cage and the bearing cage is formed from steel, and
   b) the machine element comprises a coupling device for releasable connection to a tool element, and
   c) the medical device is constructed in the form of a saw, a milling machine or a drilling machine.

20. A medical device, comprising:
   a machine element mounted so as to be linearly movable, and
   at least one linear guide, comprising at least one ball bearing and defining a longitudinal axis, for guiding a linear movement of the machine element parallel to the longitudinal axis,
   said at least one ball bearing comprising a plurality of balls which are movably held in corresponding ball holders and which guide the machine element, wherein:
      the plurality of ball holders are constructed in the form of elongated holes,
      the machine element comprises at least one rotationally symmetrical machine element section which is guided in the at least one linear guide,
      the at least one ball bearing comprises a bearing cage, and
      the plurality of ball holders are formed in the bearing cage, and
      the bearing cage comprises a radial securing device for preventing the balls from exiting from the respective ball holders in a direction away from the longitudinal axis and/or in a direction towards the longitudinal axis.

21. The medical device in accordance with claim 20, wherein the radial securing device comprises bent edges of the ball holders.

22. The medical device in accordance with claim 21, wherein the radial securing device comprises a cover sleeve, the inner diameter of which corresponds to an outer diameter of the bearing cage, and wherein the cover sleeve comprises a plurality of elongated hole-like cover through-holes, the width of which is smaller than a ball diameter, and wherein the bearing sleeve is arranged so as to surround the cover sleeve.

23. The medical device in accordance with claim 20, wherein the radial securing device comprises a cover sleeve, the inner diameter of which corresponds to an outer diameter of the bearing cage, and wherein the cover sleeve comprises a plurality of elongated hole-like cover through-holes, the width of which is smaller than a ball diameter.

24. A medical device, comprising:
   a machine element mounted so as to be linearly movable, and
   at least one linear guide, comprising at least one ball bearing and defining a longitudinal axis, for guiding a linear movement of the machine element back and forth at a high oscillation frequency parallel to the longitudinal axis,
   said at least one ball bearing comprising a plurality of balls which are movably held in corresponding ball holders and which guide the machine element, wherein:
      the plurality of ball holders are constructed in the form of elongated holes,
      the at least one ball bearing comprises a bearing cage,
      the bearing cage is arranged on the linear guide for rotation about the longitudinal axis,
      the plurality of elongated holes have a free length of movement for the ball movably arranged in each of them,
      the free length of movement corresponds to at least half of a stroke of the machine element relative to the linear guide, and
      the elongated holes have a free length of movement which is:
         at least 10% greater than half of the stroke, or
         at least 30% greater than half of the stroke.

25. The medical device in accordance with claim 24, wherein the elongated holes each define an elongated hole longitudinal axis, and wherein the elongated hole longitudinal axis extends parallel or transversely to the longitudinal axis, and wherein the elongated hole longitudinal axes include with the longitudinal axis an angle of twist in a range of from 0° to approximately 30°.

* * * * *